United States Patent [19]
Chernomorsky et al.

[11] Patent Number: 5,961,439
[45] Date of Patent: Oct. 5, 1999

[54] DEVICE AND METHOD FOR RADIATION THERAPY

[75] Inventors: Ary S. Chernomorsky, Millbrae; Robert L. Schmidlen, San Jose; Jerome Jackson, Los Altos, all of Calif.

[73] Assignee: United States Surgical Corporation, Norwalk, Conn.

[21] Appl. No.: 09/073,932

[22] Filed: May 6, 1998

Related U.S. Application Data

[60] Provisional application No. 60/077,294, Mar. 6, 1998.

[51] Int. Cl.$^6$ ....................................................... A61N 5/00
[52] U.S. Cl. ................................................................ 600/4
[58] Field of Search ............................................. 600/1–8

[56] References Cited

U.S. PATENT DOCUMENTS

| | | |
|---|---|---|
| 3,462,245 | 8/1969 | Eudes et al. ................................. 600/4 |
| 4,364,376 | 12/1982 | Bigham ....................................... 600/5 |
| 4,401,108 | 8/1983 | Gazkin et al. .............................. 600/5 |
| 5,053,019 | 10/1991 | Duffy . |
| 5,199,939 | 4/1993 | Dake et al. . |
| 5,288,285 | 2/1994 | Carter . |
| 5,302,168 | 4/1994 | Hess . |
| 5,411,466 | 5/1995 | Hess . |
| 5,472,403 | 12/1995 | Cornacchia et al. . |
| 5,529,189 | 6/1996 | Feldschuh . |
| 5,616,114 | 4/1997 | Thornton et al. . |
| 5,662,580 | 9/1997 | Bradshaw et al. . |
| 5,683,345 | 11/1997 | Waksman et al. . |
| 5,707,332 | 1/1998 | Weinberger . |

FOREIGN PATENT DOCUMENTS 9102312   8/1992   Germany .

*Primary Examiner*—John P. Lacyk

[57] ABSTRACT

There is provided a device and a method for irradiating vascular tissues. The device generally includes a transfer device having a first chamber and a second chamber and a piston slidably disposed between the chambers. A balloon catheter is provided for positioning within the vascular system and is connected to the transfer device such that an inflation lumen of the balloon catheter is in fluid communication with the second chamber. A proximal end of the balloon catheter is affixed to a mounting block which is configured to receive the transfer device. An inflation device is provided to force fluid into the first chamber such that the piston is driven to force a radioactive fluid contained in the second chamber into the balloon.

21 Claims, 14 Drawing Sheets

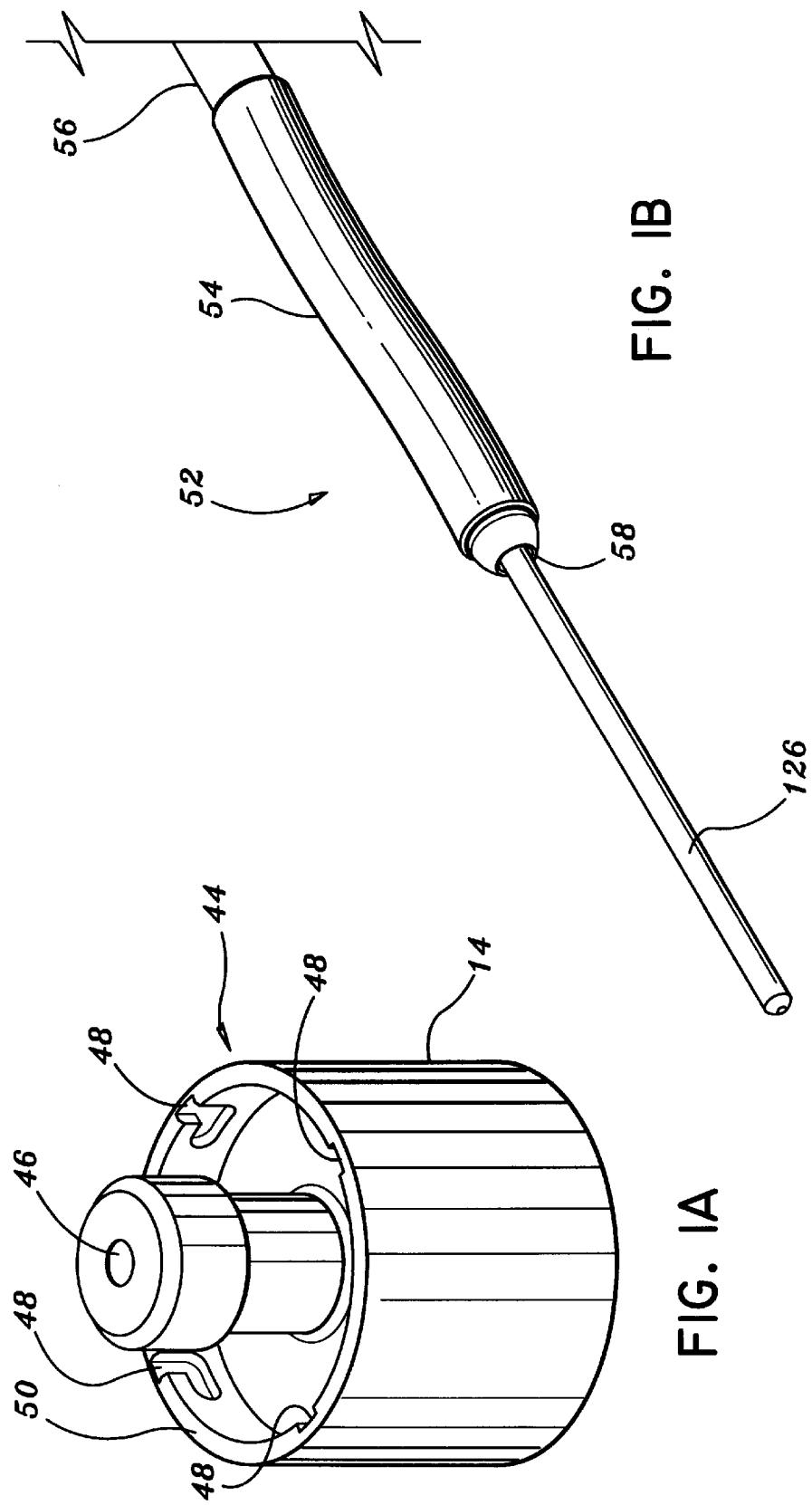

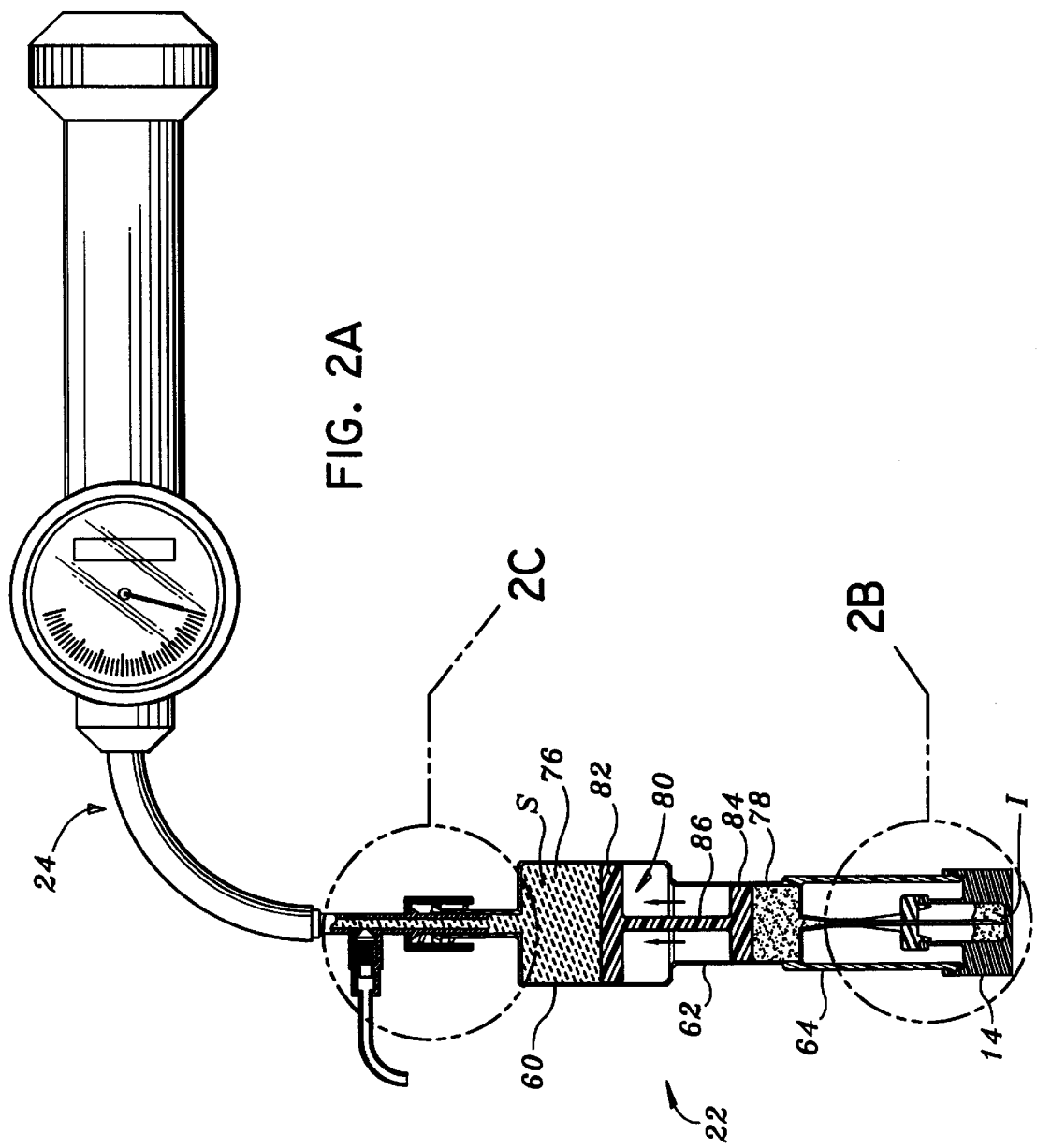

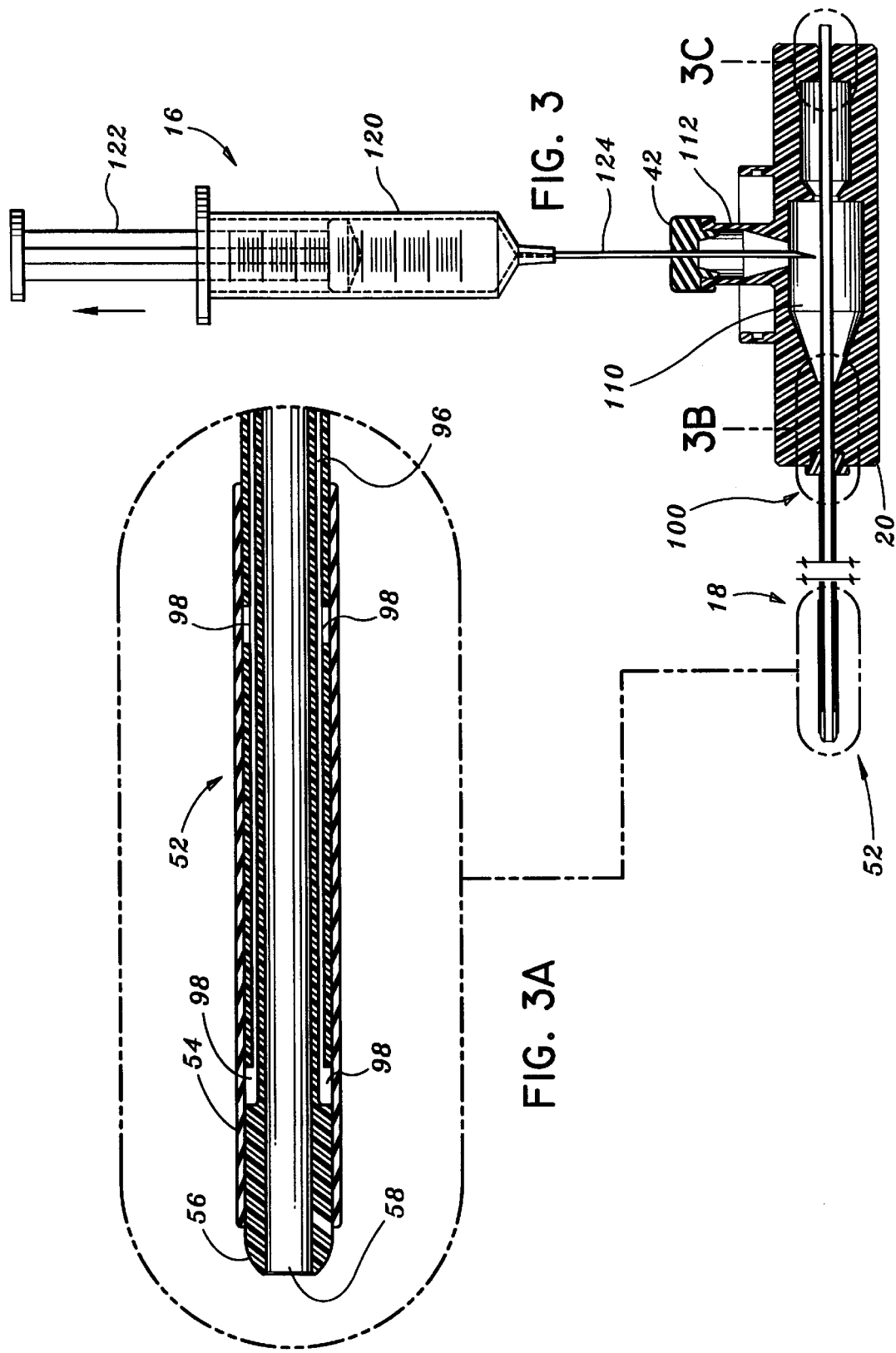

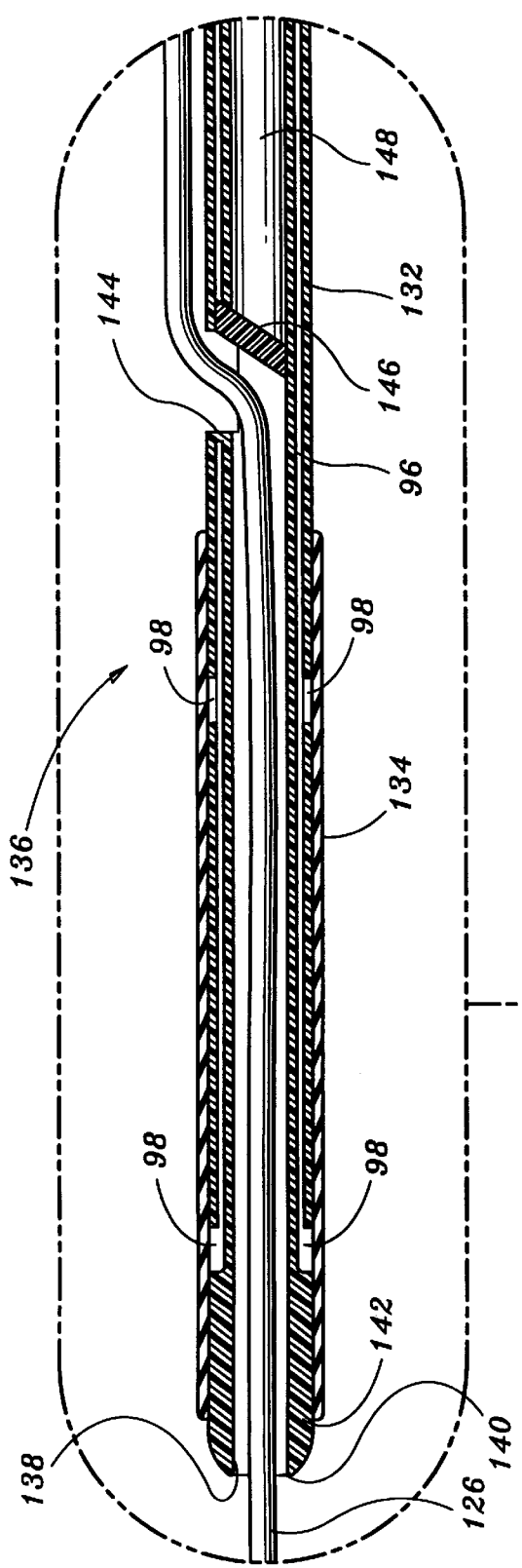
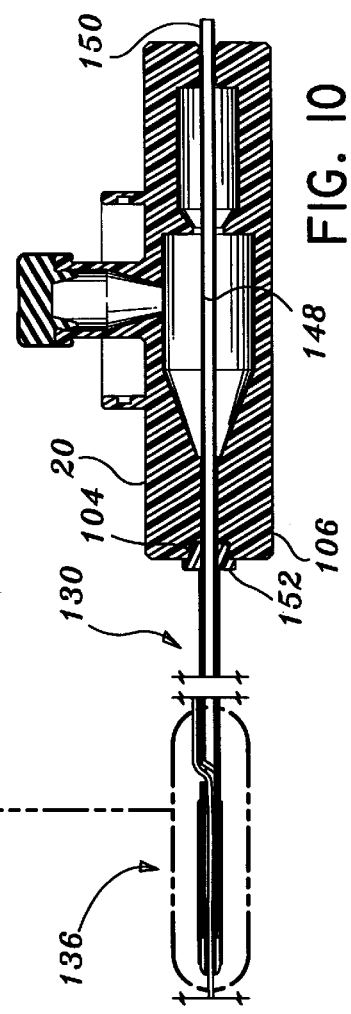
FIG. 10A
FIG. 10

DEVICE AND METHOD FOR RADIATION THERAPY

CROSS REFERENCE TO RELATED APPLICATIONS

This application claims priority to U.S. Provisional Application Serial No. 60/077,294, filed on Mar. 6, 1998, entitled "Device and Method for Radiation Therapy," the entire contents of which are incorporated herein by reference.

1. Technical Field

The technical field relates generally to the use of radiation therapy after an angioplasty procedure, to minimize the occurrence of restenosis and, more particularly, to a device and method for delivering a radio isotope to a stenotic region, e.g., in liquid or gaseous form, to inhibit restenosis.

2. Description of the Related Art

A common treatment for blockage or stenosis of the arteries is a procedure known as percutaneous transluminal angioplasty (PTA) and, when utilized within the coronary artery, is known as percutaneous transluminal coronary angioplasty (PTCA). During this procedure, the location of a stenotic constriction or blockage within the coronary artery is identified and a guide wire is advanced through the vascular system to a point distal to or beyond the blockage. Subsequently, an angioplasty catheter in one form having an inflatable angioplasty dilatation balloon at a distal end thereof or in a second form an atherectomy catheter, or a stent delivery catheter, is advanced along the guide wire until the balloon is located at the point of constriction. The balloon is then repeatedly inflated and deflated to open the constriction by compressing the plaque against the vessel walls. In this manner, a constriction within the vascular system may be opened to allow increased blood flow. Similarly, the plaque can be removed by atherectomy, or the plaque can be scaffolded by placing a stent.

The vascular tissue may respond to the trauma by proliferative growth of cells responsible for restenosis, e.g., smooth muscle tissue cells, and deposition of extracellular matrix material. Upon increased growth of such cells, formerly constricted area may become reconstricted or narrowed down, which is commonly referred to as "restenosis." This can occur any time from within a few weeks to several years following the original angioplasty procedure, thus, often necessitating repeated angioplasty procedures to reopen the constriction. Other causes of restenosis have been reported including, but not limited to, elastic recoil of the vessel wall and focal shrinkage of the vessel wall, commonly referred to as "negative remodelling."

It has been found that by exposing the vascular tissues to radiation subsequent to the balloon angioplasty procedure, the proliferative growth of the smooth muscle cells and/or vessel shrinkage responsible for restenosis is inhibited. However, difficulty in providing uniform radiation to the surrounding tissue may arise. Often, after expansion of a constricted area by a balloon angioplasty procedure, the resulting relatively unconstricted area has a generally asymmetrical cross-section. The asymmetrical cross-section may pose problems for those devices which are configured to position a radioactive source substantially at the center of the vascular structure. Thus, it would be desirable to have a device and method for delivering a radioactive dose in a substantially uniform manner to the site of a vascular constriction post-angioplasty.

SUMMARY

There is provided a device and a method of irradiating vascular tissues which have been subjected to a balloon angioplasty procedure. The device generally includes a balloon catheter having an expandable balloon which can be positioned over a guide wire within the vascular tissue, a transfer device for transferring radioactive material, e.g., fluid, from the transfer device to the balloon and an inflation device for forcing the radioactive fluid out of the transfer device and into the balloon. The balloon catheter includes an inflation lumen extending from an interior of the balloon through the catheter to a proximal portion of the catheter. The balloon catheter also includes a guide wire lumen. The guide wire lumen may extend the entire length of the catheter from its distal to its proximal end or may extend from the distal end to a point just proximal of the balloon. The transfer device includes first and second chambers which are separated by a movable piston or membrane. The first chamber is configured to receive a fluid to move the piston within the transfer device while the second chamber is configured to receive, retain and shield or isolate the radioactive fluid prior to injection into the balloon catheter. The inflation device provides a fluid, preferably saline, to the first chamber to move the piston by creating a positive or negative gauge pressure in the first chamber. Preferably, the inflation device may include a pressure gauge as well as an overpressure relief valve. As used herein, the term "radioactive fluid" is intended to encompass liquids, gases, solids and/or combinations thereof.

A mounting block may also be provided to connect the second chamber of the transfer device to the inflation lumen of the balloon catheter. Specifically, the mounting block retains the proximal end of the balloon catheter with the inflation lumen in fluid communication with the second isotope containing chamber in the mounting block. The mounting block includes an injection port having a self-sealing septum which is in fluid communication with the second isotope containing chamber.

In one embodiment, the mounting block is interlocked to the proximal end of the balloon catheter by use of a bayonet style fitting. It is further contemplated that other interlocking optical, mechanical and/or electrical features and/or structures may be provided, and may include recognition features to ensure that only a catheter suitable for radiation therapy is coupled to the transfer device. Moreover, such recognition features and/or structures may provide information to an associated system to identify to the system characteristics of the catheter, e.g., catheter length and size, capacity, etc., which may be used in controlling the transfer device to assure transfer of an appropriate quantity of isotope containing material to the balloon catheter. The system may calculate, display and/or control treatment time and dose delivery and may monitor system integrity, e.g., using fluid pressure sensors in the catheter, second chamber or mounting block.

The transfer device includes an injection needle which extends from the second chamber and is provided to pierce self-sealing septum in order to draw and inject the radioactive fluid through the self-sealing septum. Preferably, the injection needle is provided with an elastomeric boot surrounding the needle which acts as a seal against the septum. The transfer device may also be provided with a needle shield extending from the second chamber and surrounding the injection needle. The transfer device may be connected to the mounting block by suitable means such as a bayonet style mounting fixture.

There may also be provided a separate source or container for the radioactive fluid which also has a self-sealing septum. The source will also include a bayonet style mounting fixture for affixing to the transfer device in order to load the transfer device with the radioactive fluid. Additionally, an aspiration syringe may be provided having a needle to pierce the septum of the mounting block in order to draw air out of the balloon and inflation lumen of the balloon catheter to create a vacuum therein.

There is also disclosed a method for irradiating vascular tissues which includes providing a transfer device having first and second chambers and a piston movably disposed within the chambers, an inflation device for moving the piston within the first and second chambers and a balloon catheter for carrying a radioactive fluid from the second chamber of the transfer device to a balloon on a distal end of the balloon catheter. The method includes loading radioactive fluid into the second chamber of the transfer device, positioning the balloon at a stenotic region within the vascular system, attaching the transfer device to a proximal portion of the balloon and attaching an inflation device to the transfer device such that the inflation device can force fluid into the first chamber of the transfer device. The method further includes forcing fluid from the inflation device into the transfer device to force the piston to force the radioactive fluid out of the second chamber of the transfer device and into the balloon to substantially fill the balloon thereby irradiating surrounding tissues with the radioactive fluid. The method may further include the step of removing air from the balloon catheter prior to the step of inserting the catheter in the vascular system.

BRIEF DESCRIPTION OF THE DRAWINGS

Various embodiments are described herein with reference to the drawings wherein:

FIG. 1A is a perspective view of a radiation fluid source container;

FIG. 1B is an enlarged perspective view of the distal end of a treatment catheter associated with the system of FIG. 1;

FIG. 2A is a side elevational view, partially shown in section, illustrating the assembled inflation device, transfer device and radiation fluid source container of the system of FIG. 1;

FIG. 3 is a side view, partially shown in section, of the balloon catheter, mounting block and aspiration syringe of FIG. 1;

FIG. 3A is an enlarged sectional view of the distal end of the balloon catheter of FIG. 3;

FIG. 7 is a side elevational view, partially shown in section, of the assembled inflation device, transfer device and mounting block;

FIG. 7A is an enlarged view illustrating injection of radioactive fluid from the transfer device to the mounting block;

FIG. 10 is an elevational cross-section view of a rapid exchange style catheter for use with the system of FIG. 1; and FIG. 10A is an enlarged view of the distal end of the balloon catheter of FIG. 10.

DETAILED DESCRIPTION OF THE PREFERRED EMBODIMENTS

Figure 1:
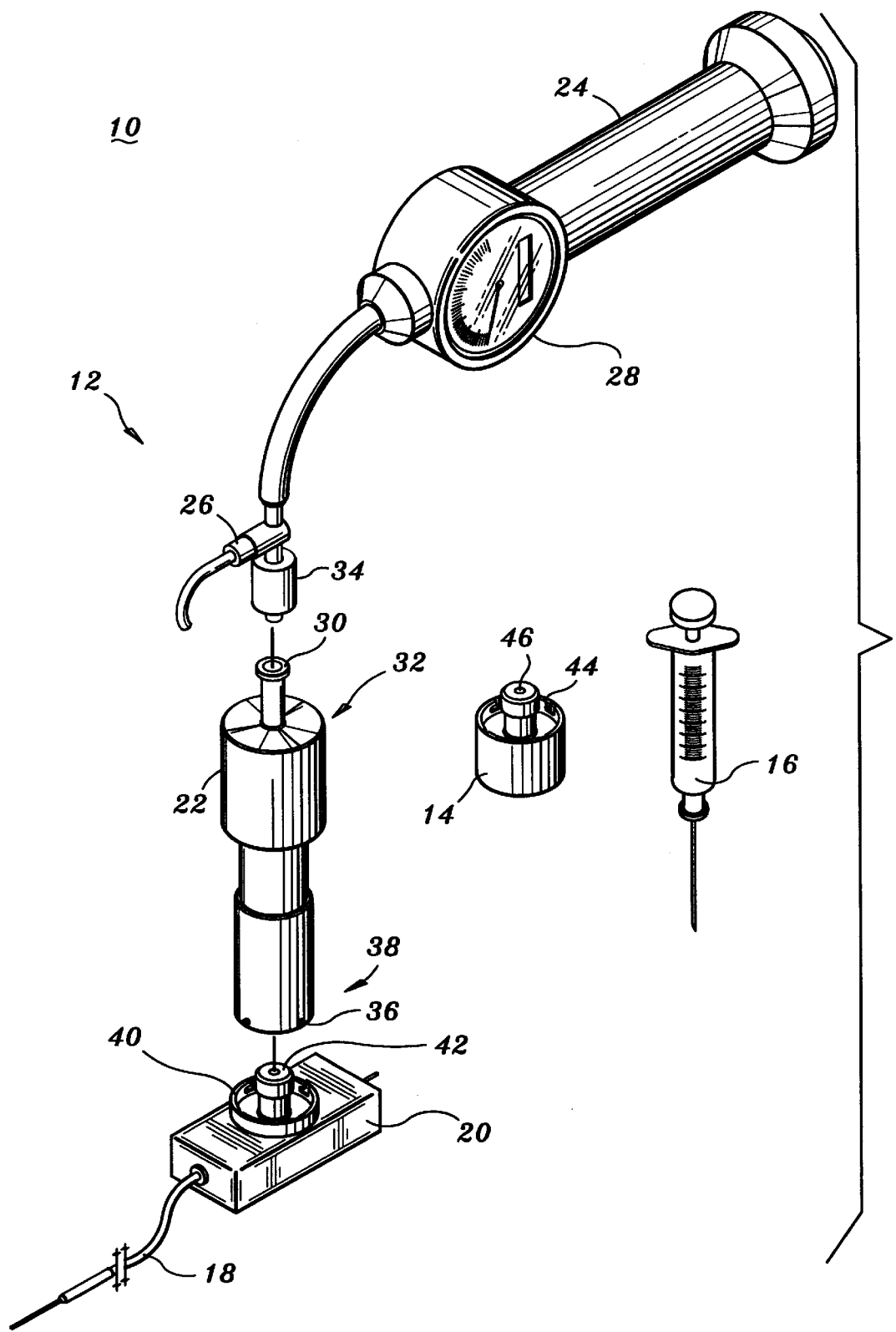
FIG. 1 is a perspective view of a system for providing a fluid radiation therapy treatment.

Referring to FIG. 1, there is disclosed a preferred embodiment of a system 10 for radiation therapy. System 10 is particularly configured to deliver a source of radioactive fluid to a treatment balloon which has been positioned within a vascular system at the site of a previous angioplasty procedure. System 10 generally includes a device for radiation therapy 12, a container such as a vial or other source of radioactive fluid 14, and an aspiration syringe 16. Device for radiation therapy 12 includes a balloon catheter 18 which extends from a mounting block 20. A transfer device 22 is removably engagable with mounting block 20. There is also provided an inflation device 24 which is removably engagable with transfer device 22. Inflation device 24 is provided to force radioactive fluid out of transfer device 22 and through mounting block 20 into balloon catheter 18. Preferably, a pressure relief valve 26 may be positioned between inflation device 24 and transfer device 22 to prevent over expansion of balloon catheter 18.

Inflation device 24 is of known type utilized in balloon angioplasty procedures and may include a pressure gage 28 to monitor the exact pressures. This is particularly preferable in the present radiation treatment procedure where it is not necessary to reach high pressures within the balloon catheter, but rather to merely expand the balloon to the point that it contacts surrounding tissue and plaque.

In order to connect transfer device 22 to inflation device 24, transfer device 22 is provided with a flange 30 at a proximal end 32 thereof. Flange 30 is engagable with a threaded coupling 34 associated with inflation device 24. Similarly, to connect transfer device 22 to mounting block 20, transfer device 22 is provided with the male half of a "bayonet-type" or "luer" fitting 36 at a distal end 38 thereof. The male half of the bayonet or luer fitting 36 is engagable with a female half of a bayonet or luer fitting 40 positioned on mounting block 20. As used herein, the term proximal refers to that portion of the device closer to the user while the term distal refers to that part of the device further from the user. In order to prevent leakage of radioactive fluid during transfer from transfer device 22, mounting block 20 is preferably provided with a self-sealing elastic septum 42 which is in fluid communication with balloon catheter 18.

To facilitate loading of the radioactive fluid into transfer device 22, source 14 also includes a female half of a bayonet or luer fitting 44 which is engagable with the male half of the bayonet or luer fitting 36 on transfer device 22. Additionally, source 14 also includes a self-sealing elastic septum 46 to prevent inadvertent leakage of radioactive fluid.

Referring now to FIG. 1A, it can be seen that the bayonet style fitting 44 on source 14 is of known variety including a plurality of L-shaped slots 48 formed within a circumferential flange 50. It is contemplated that other locking structures such as, e.g., luer locks, may be substituted for the bayonet-style fitting 44. Self-sealing septum 46 projects a predetermined distance above flange 50. Referring for the moment to FIG. 1B, it can be seen that a distal end 52 of balloon catheter 18 generally includes an elastomeric sleeve or balloon 54 mounted on a catheter shaft 56. Balloon catheter 18 may be configured as either an over the wire (OTW) type catheter or a rapid exchange "RE" catheter. When an OTW style catheter is used with device 12 for radiation therapy, a guide wire lumen 58 extends generally throughout the length thereof for receipt of a guide wire 126 as described hereinbelow.

Figures 1C, 1D:
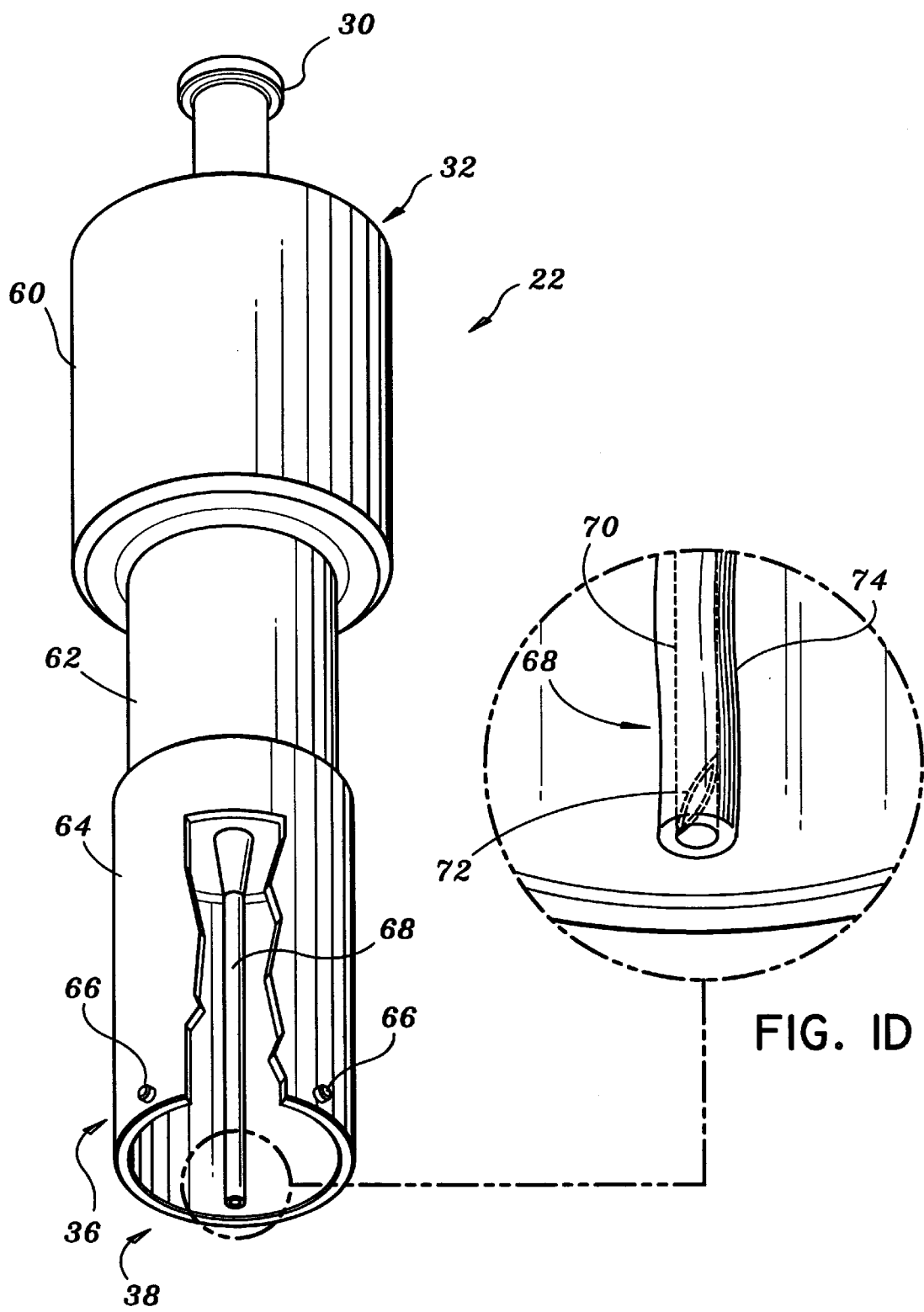
FIG. 1C is a perspective view, partially shown in section, of a transfer device associated with the system of FIG. 1.
FIG. 1D is an enlarged view of a booted needle of the transfer device of FIG. 1C.

Referring now to FIG. 1C, it can be seen that transfer device 22 includes an enlarged saline housing 60 and a radioactive fluid housing 62 extending from extended large saline housing 60. A needle shield 64 extends distally from radioactive fluid housing 62 and is provided with a plurality of projections 66 which form the male half of the bayonet fitting 36 on distal end 38 of transfer device 22. As noted above, flange 30 is provided at proximal end 32 of transfer device 22 for engagement with inflation device 24. In order to transfer radioactive fluid between transfer device 22 and self-sealing septum 42 of mounting block 20 or self-sealing septum 46 of source 14, transfer device 22 is provided with a booted needle 68 provided within needle shield 64. Booted needle 68 extends distally from radioactive fluid housing 62. Referring for the moment to FIG. 1D, booted needle 68 generally includes an inner needle 70 having a sharply pointed tip 72 which is configured to pierce elastomeric self-sealing septums 42 and 46. Needle 70 may be formed of any suitable material, for example, stainless steel. Booted needle 68 further includes an elastomeric sleeve or boot 74 which surrounds needle 70. Boot 74 is provided to further shield pointed tip 72 of needle 70 and to serve as a further seal against a septum to prevent inadvertent release of radioactive fluid when fluid is being drawn into or forced out of needle 70 or when the system is disconnected.

Figure 2:
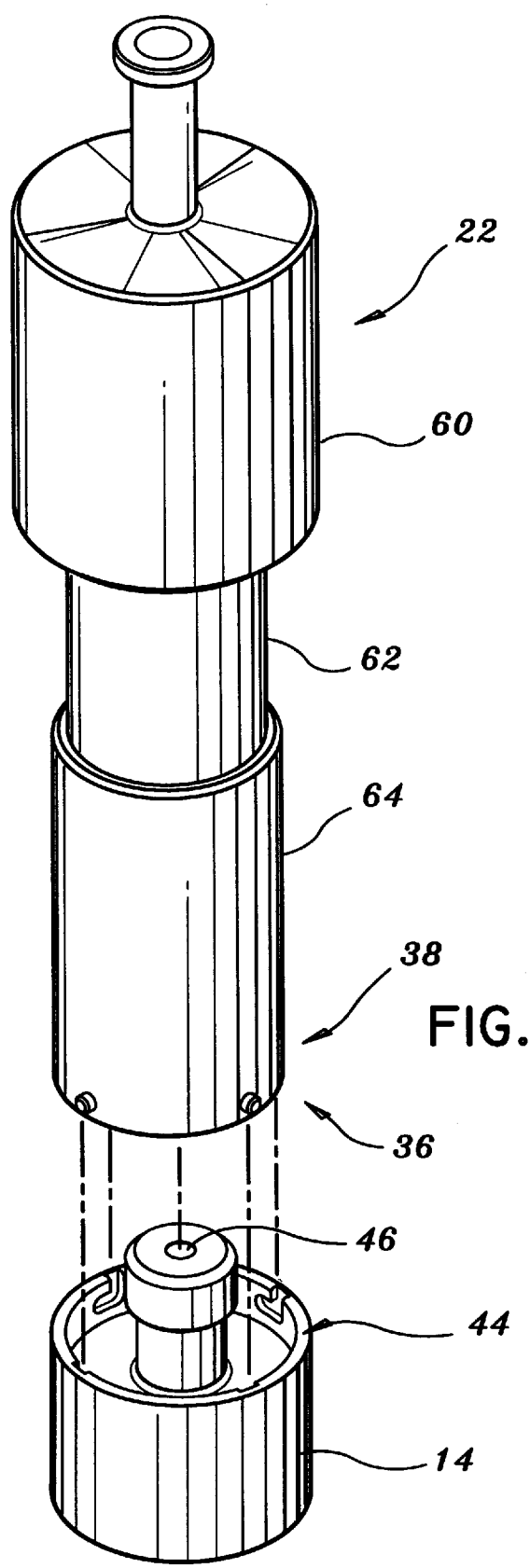
FIG. 2 is a perspective view of the transfer device and radiation fluid source container.

Referring to FIG. 2, in order to load the radioactive fluid from source 14 into transfer device 22, transfer device 22 is positioned such that male bayonet 36 at the distal end 38 thereof is brought into engagement with the female bayonet fitting 44 on source 14. As transfer device 22 is brought into engagement with source 14, booted needle 70 (FIG. 1D) is brought into engagement with and pierces self-sealing septum 46.

Figure 2C:
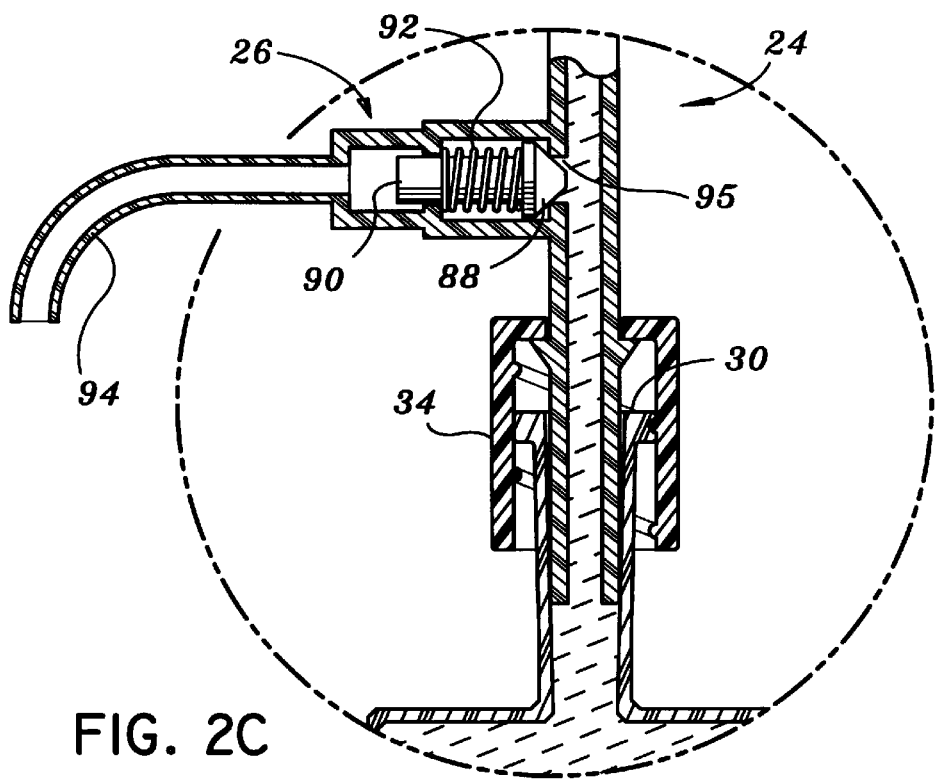
FIG. 2C is an enlarged view illustrating engagement of the inflation device with the transfer device as well as a pressure relief valve associated with the inflation device.
Figure 2B:
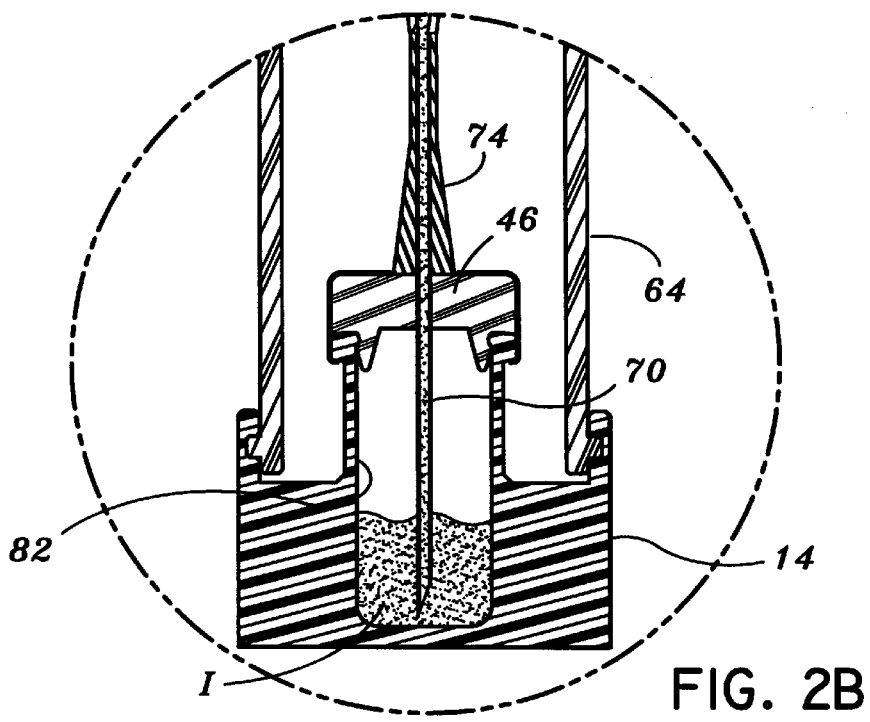
FIG. 2B is an enlarged side view, shown in section, illustrating engagement of the transfer device with the fluid source container.

Referring now to FIG. 2B, the construction of transfer device 22 will now be described. Enlarged saline housing 60 defines an internal saline chamber 76 for receipt of saline fluid S from inflation device 24. Similarly, radioactive fluid housing 62 defines an interior isotope chamber 78 for receipt of the radioactive fluid or isotope I from source 14. The isotope I is stored in isotope chamber 78 until it is forced out into balloon catheter 18 during use. In order to move the isotope fluid I out of or into isotope chamber 78, there is provided a piston 80 movably positioned within chambers 76 and 78. Piston 80 includes an enlarged piston head 82 positioned within saline chamber 76 and a smaller piston head 84 which is movably positioned within isotope chamber 78. A piston shaft 86 connects piston heads 82 and 84. It should be noted that the particular dimensions of piston head 82 and piston head 84 may be varied in order to produce desired magnification or reduction of relative fluid pressure between saline fluids in saline chamber 76 and isotope fluid I in isotope chamber 78. Also, it should be noted that if saline chamber 76 and isotope chamber 78 are of the same diameter then piston heads 82 and 84 can be replaced with a single piston.

Referring further to FIG. 2B, it can be seen that source 14 defines an internal isotope chamber 78 which contains a quantity of radio active isotope I. Radio active isotope I is a beta or gamma emitting radio isotope and is preferably 50–100 millicuries of RE 188 which may be easily generated at hospitals and is readily available. A preferred radio active isotope is thus provided in liquid form and generally has a relatively short half life. However, safety precautions need be maintained to prevent contamination of the interventional cardiology laboratory. As shown, when needle shield 64 is engaged with source 14, needle 70 is forced through self-sealing septums of boot 74 and septum 46. Self-sealing septum 46 provides a fluid tight seal about needle 70. Additionally, elastomeric boot 74 is compressed against elastomeric septum 46 and provides a further seal therebetween. Referring for the moment to FIG. 2B, in order to fill transfer device 22 with isotope I, inflation device 24 is engaged with transfer device 22 in a manner described hereinabove and is further illustrated in FIG. 2C. Saline chamber 76 is initially completely filled with saline fluid S. Thereafter, transfer device is engaged with source 14 in a manner described hereinabove such that needle 70 punctures the elastomeric septum 46 and is in contact with isotope I. At this point, negative pressure is provided by inflation device 24 to draw saline out of saline chamber 76. Upon drawing saline fluid S out of saline chamber 76, piston 80 is drawn proximally within transfer device 22 thereby forming a vacuum in isotope chamber 78. The vacuum created in isotope chamber 78 draws the isotope I from chamber 82 and source 14 into chamber 78 in transfer device 22. Once a predetermined quantity of isotope I has been received within chamber 78 of transfer device 22, transfer device 22 and source 14 may be rotated to disengage their bayonet fittings. Pulling source 14 away from transfer device 22 draws needle 70 through self-sealing septum 46 which thereafter seals about itself preventing any further release of radioactive isotope I from source 14. In this manner, transfer device 22 is loaded with a predetermined amount of isotope I. Preferably, this procedure takes place inside a radiation laboratory. Once transfer device has been loaded with isotope I, it may be retained within a shielded container or safe for transport to the interventional cardiology laboratory prior to use.

Referring for the moment to FIG. 2C, and as noted above, inflation device 24 is provided with a pressure relief valve 26. Pressure relief valve 26 is of known variety and generally includes a seal 88 having a shaft 90 extending therefrom. A spring 92 is provided about shaft 90 and biases seal 88 into engagement with fluid opening 95 in inflation device 24. Spring 92 is of a predetermined resistance such that when the fluid pressure within inflation device 24 exceeds a predetermined amount, seal 88 allows fluid to flow from inflation device 24 and out through a drain tube 94 thereby relieving any excess pressure within device for radiation therapy 12.

Referring now to FIG. 3, the details of the mounting block 20 and balloon catheter 18 will now be described. As shown, balloon catheter 18 extends distally from mounting block 20.

Referring to FIG. 3A, the illustrated balloon catheter 18 is of the over the wire variety including a catheter shaft 56 defining a guide wire lumen 58 extending completely therethrough. As noted above, a balloon 54 is affixed to a distal end 52 of balloon catheter 18 and is mounted on catheter shaft 56. It should be noted that balloon 54 may be formed from an elastic or inelastic material. The balloon 54 may act solely as means to deliver the radiation therapy or it may provide a dilatation function within a vascular system. In either case, it as a chamber for radioactive fluid to provide uniform irradiation of the surrounding vascular tissue. Balloon catheter 18 includes a balloon inflation lumen 96 formed within catheter shaft 56. Preferably, inflation lumen 96 is concentric with guide wire lumen 58. A plurality of inflation ports 98 provide fluid communication between the inflation lumen 96 and an interior surface of balloon 54. Inflation lumen 96 extends from inflation ports 98 approximately to a mid-portion 100 (FIG. 3) of mounting block 20.

Figure 3B:
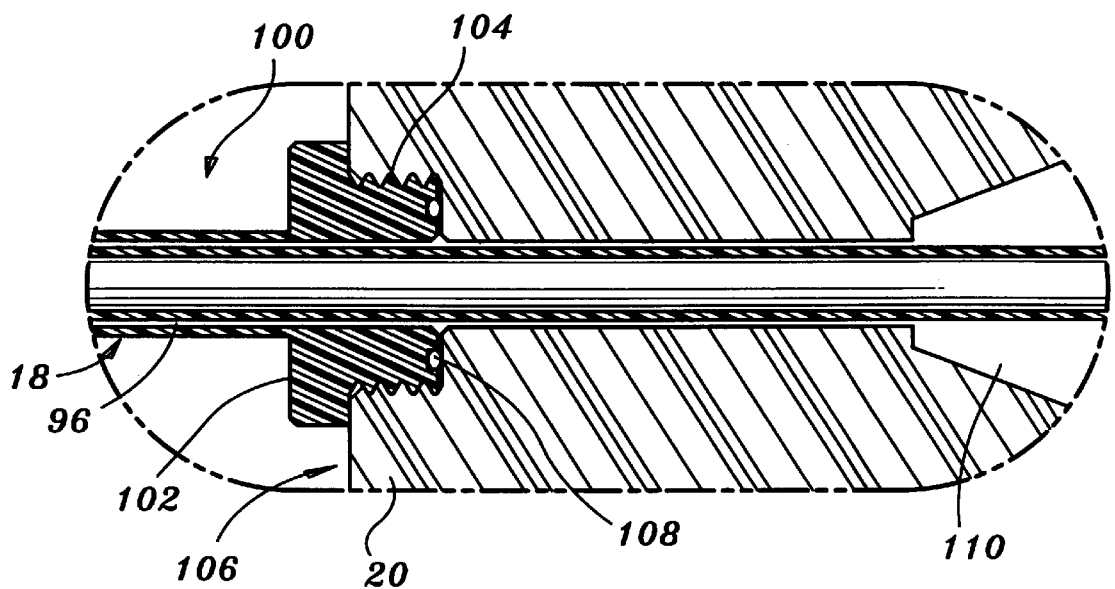
FIG. 3B is an enlarged view of the distal end of the mounting block associated with the catheter of FIG. 3.

As shown in FIG. 3B, catheter 18 is preferably secured to mounting block 20 by means of a threaded cap 102 at mid portion 100 which engages threads 104 formed in a distal end 106 of mounting block 20. The particular balloon catheter 18 illustrated is of a variety specifically configured to engage mounting block 20. However, it is also contemplated that standard configuration balloon catheters may be utilized with the present system requiring only minor modifications, as will be readily apparent to those skilled in the art, to the utilized catheter and mounting block 20. A circular seal or "O" ring 108 is provided between threaded cap 102 and mounting block 20 to provide a fluid tight seal between catheter 18 and mounting block 20. As shown, the inflation lumen 96 continues through mounting block 20 into an interior chamber 110 formed in mounting block 20.

Referring to FIG. 3, as shown, chamber 110 is in fluid communication with an injection port 112. Self sealing septum 42 is preferably mounted onto injection port 112. Thus, any air to be aspirated out of catheter 18 or any isotope to be injected into catheter 18 will be drawn through inflation lumen 96, chamber 110 and injection port 112 by means of a needle penetrating self sealing septum 42.

Figure 3C:
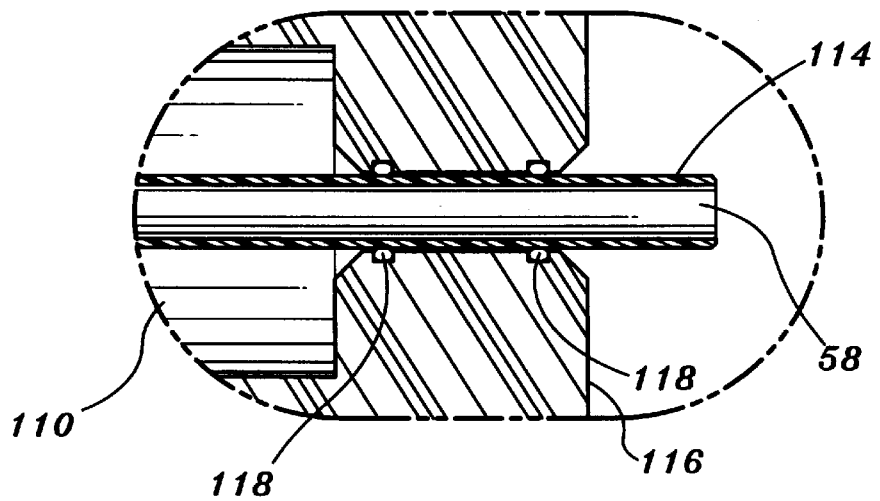
FIG. 3C is an enlarged view of the proximal end of the mounting block associated with the catheter of FIG. 3.

Referring now to FIG. 3C, a proximal end 114 of catheter 18 extends out a proximal end 116 of mounting block 20. Thus, mounting block 20 additionally serves as a "handle" for manipulation of balloon catheter 18 along a guide wire. As shown, a plurality of "O" rings 118 are provided between proximal end 114 of catheter shaft 56 and an inner surface of proximal end 116 of mounting block 20 to provide a fluid tight seal.

Referring back to FIG. 3, aspiration syringe 16 is of known variety and generally includes a syringe body 120 having a plunger 122 slidably mounted therein. A syringe needle 124 extends from syringe body 120. In utilizing balloon catheter 18 to deliver an isotope fluid to a selected site, it is necessary to avoid problems with irregular dosimetry by providing a vacuum within balloon catheter 18. Thus, in order to prepare balloon catheter 18 for use, aspiration syringe 16 is advanced toward mounting block 20 such that syringe needle 124 pierces self sealing septum 42 and enters chamber 110 of mounting block 20. Plunger 122 is drawn to provide approximately a 60 cc vacuum on catheter 18 for about 10 seconds. Upon removal of aspiration syringe 16 from mounting block 20, self sealing septum 42 seals about itself thereby retaining the vacuum within the assembled balloon catheter 18 and mounting block 20.

Figure 4:
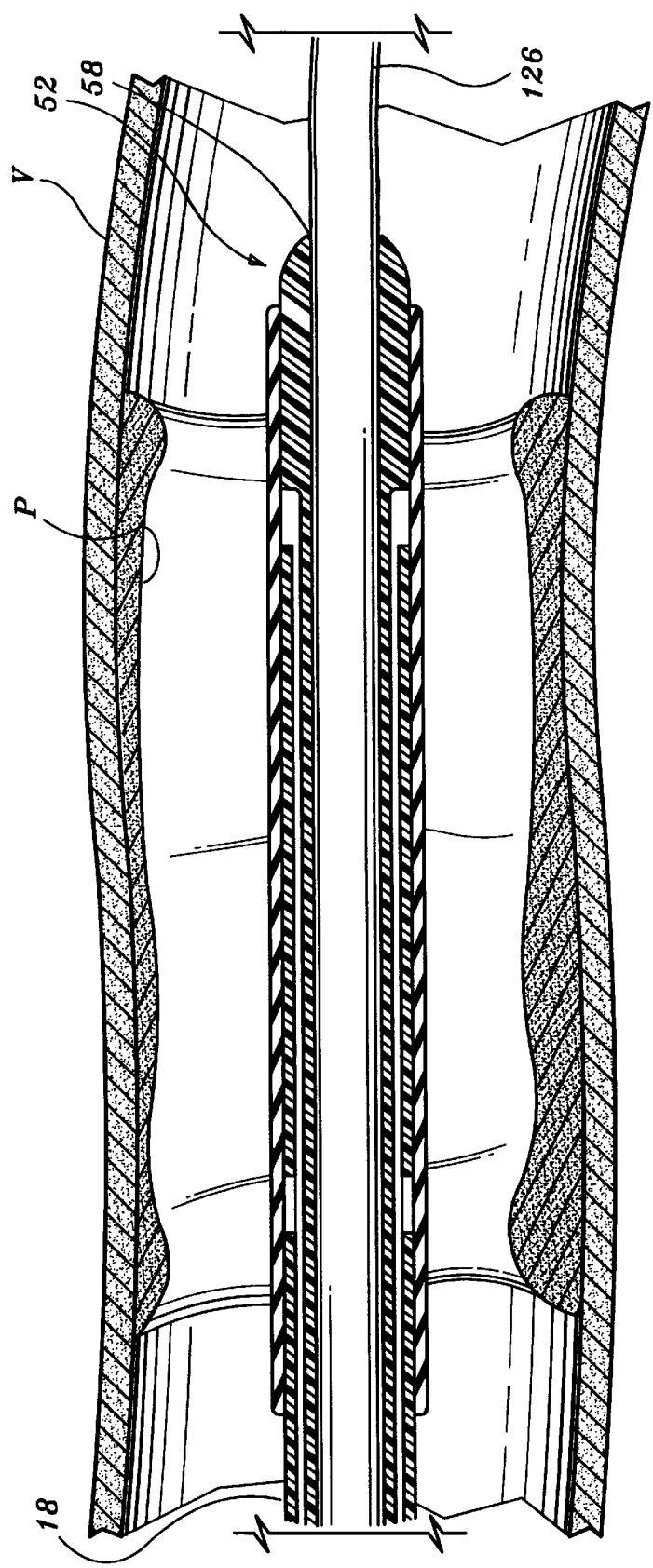
FIG. 4 is a side view, shown in section, of the distal end of the balloon catheter of FIG. 1, inserted into a vascular system over a guide wire and positioned at a location of an expanded stenotic region.
Figure 5:
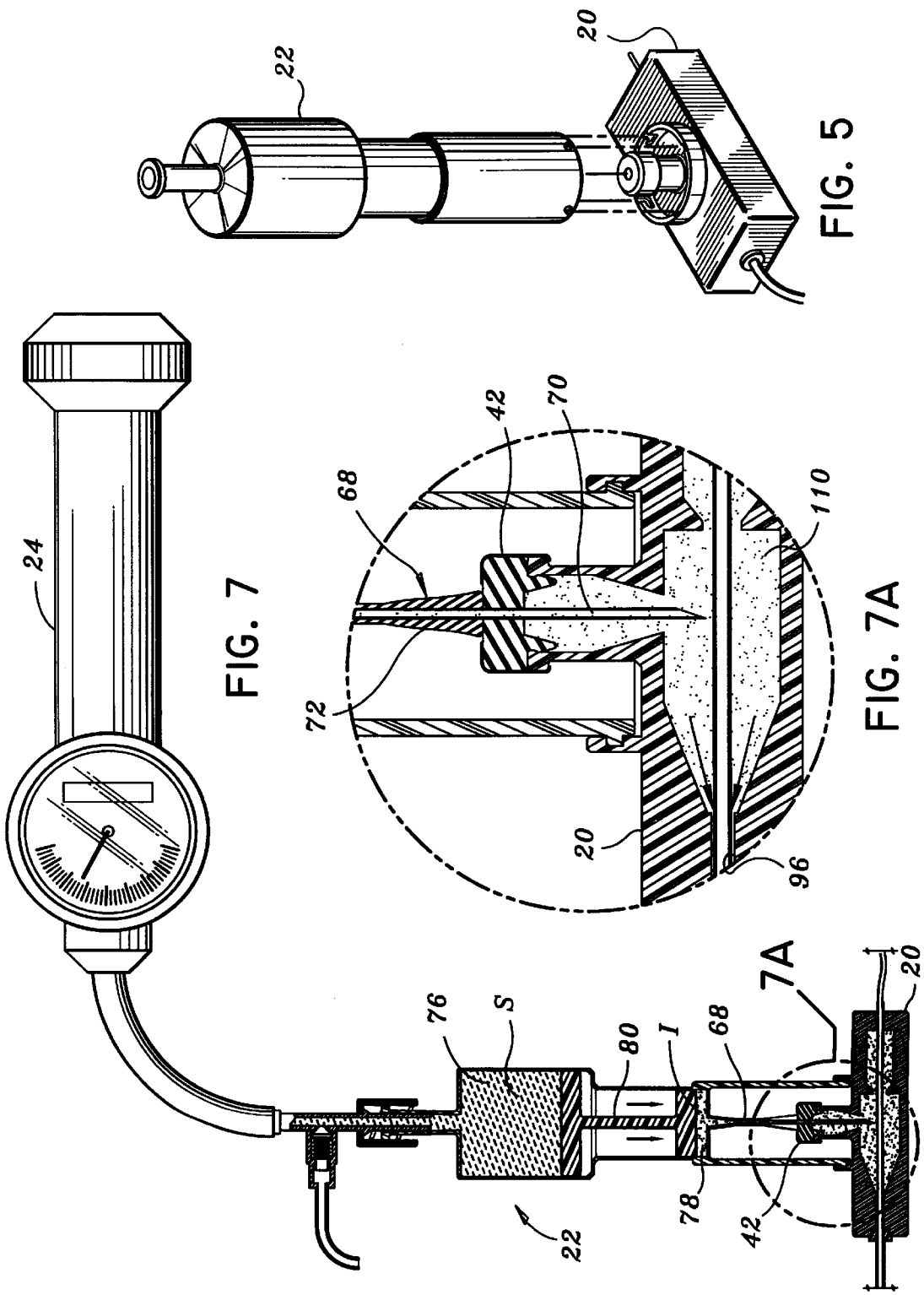
FIG. 5 is a perspective view of the transfer device being moved into engagement with the mounting block.
Figure 6:
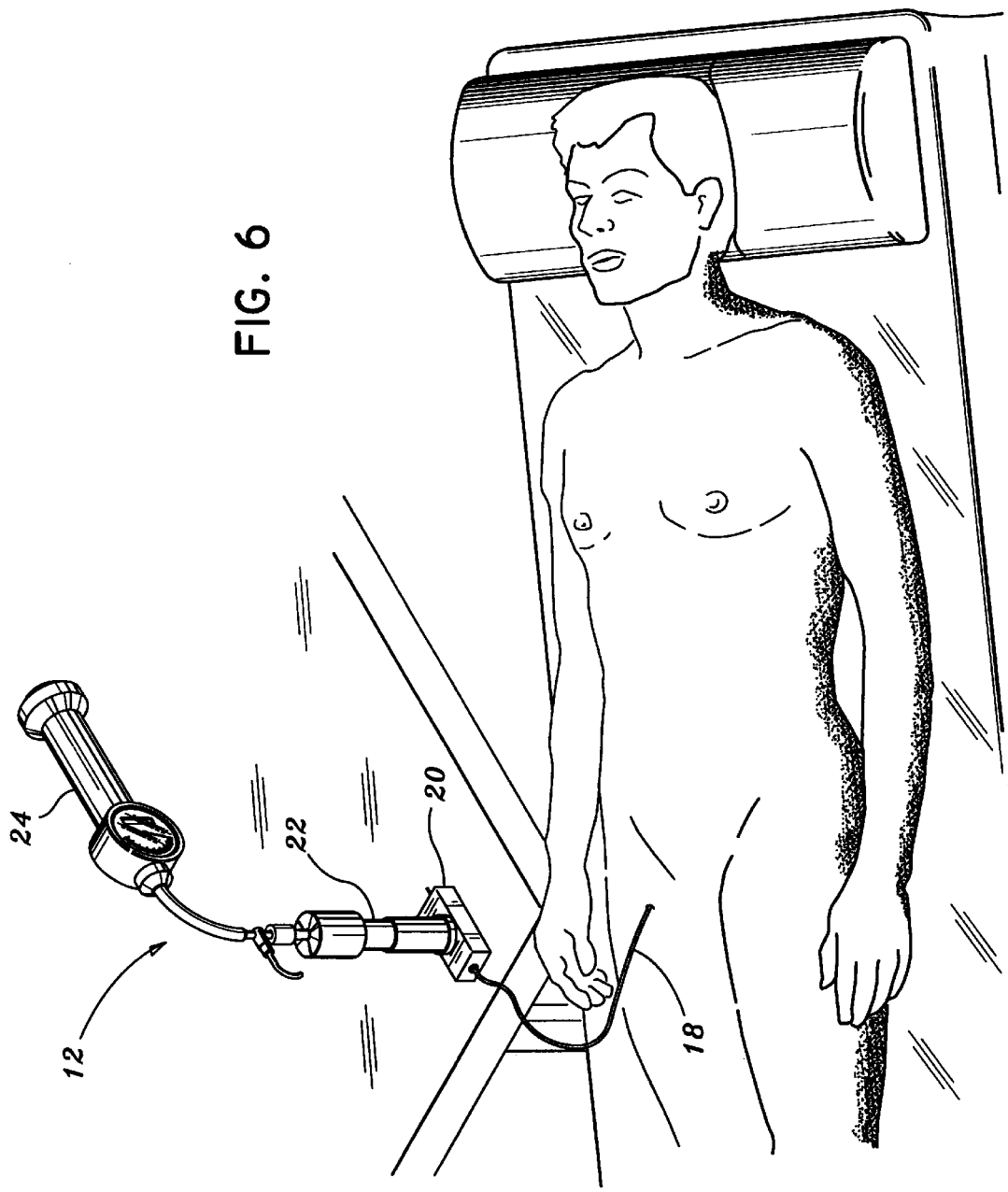
FIG. 6 is an enlarged perspective view of the device for radiation therapy of FIG. 1 with the balloon catheter inserted into a patient.

Referring to FIG. 4, after an angioplasty procedure has been performed, the angioplasty dilatation balloon is removed from a patient leaving a guide wire 126 in place and extending down to the now expanded stenotic region of a vessel V having compressed plaque P. A proximal end of guide wire 126 may be inserted into guide wire lumen 58 at distal end 52 of balloon catheter 18 and balloon catheter 18 maneuvered to the constricted site along guide wire 126. Once balloon catheter 18 has been positioned within a patient (FIG. 6.), fluid transfer device 22 containing isotope I may be engaged with mounting block 20 in a manner described hereinabove (FIG. 5).

Referring to FIGS. 7 and 7A, upon engagement of fluid transfer device 22 with mounting block 20, booted needle 68 of fluid transfer device 22 engages self sealing septum 42 of mounting block 20. As shown, needle 70 pierces self sealing septum 42 while elastomeric boot 72 expands to provide an additional seal against self sealing septum 42. Inflation device 24 may then be affixed to transfer device 22 in a manner described hereinabove and activated to a known predetermined pressure to drive saline into saline chamber 76 thereby forcing piston 80 to compress isotope I contained in isotope chamber 78 and force isotope I through needle 70 into chamber 110. Isotope I forced through chamber 110 is unimpeded by air due to the vacuum created within the inflation chamber 110 and isotope I is forced into inflation lumen 96.

Figure 8:
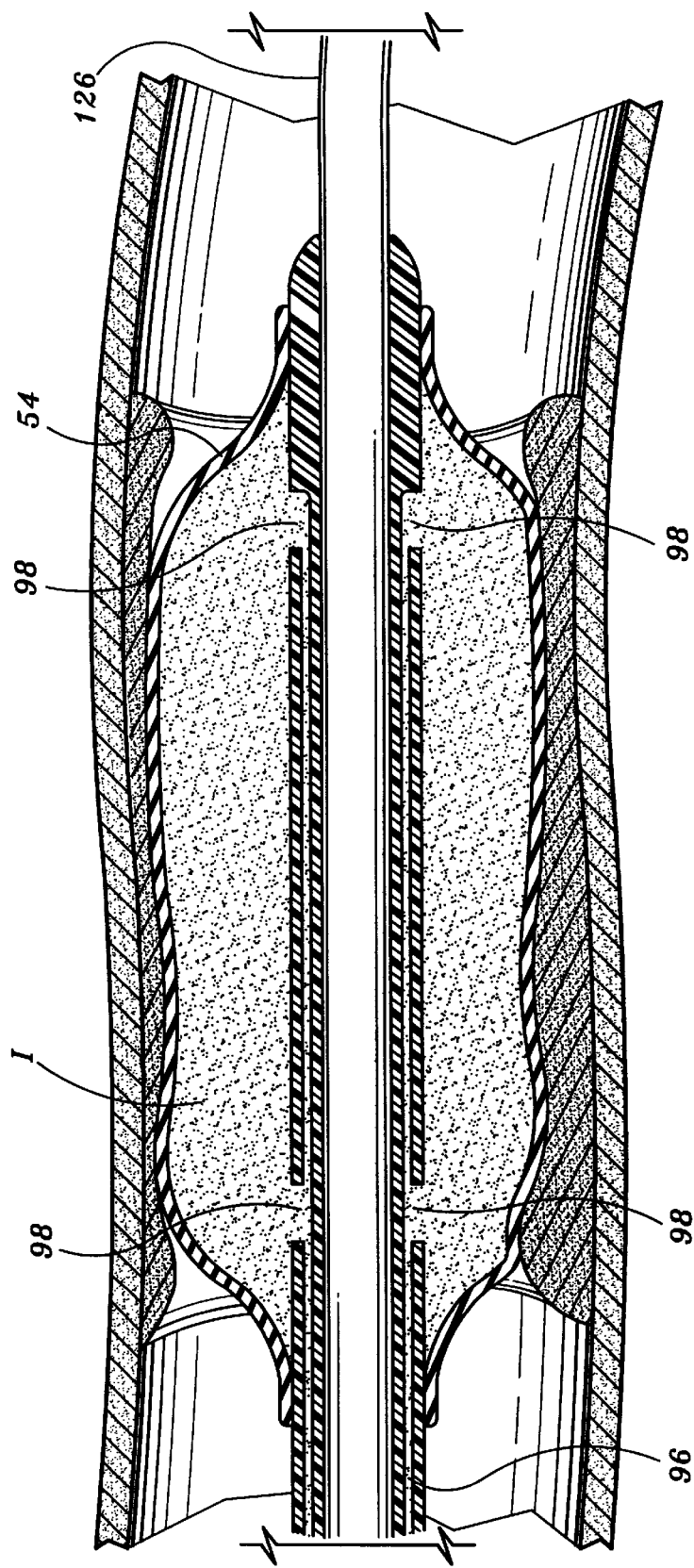
FIG. 8 is a side view, shown in section, illustrating expansion of the balloon at the distal end of the catheter by the radioactive fluid and into contact with the surrounding tissue.

Referring now to FIG. 8, as isotope I is forced through inflation lumen 96, it passes through inflation ports 98 into an interior of balloon 54 thereby expanding balloon 54 into contact with the compressed plaque P and any other exposed vascular tissue V within the vascular system at the operative site. As noted above, balloon 54 may be formed as an elastic or inelastic balloon. In either event, pressures are maintained at sufficiently low levels such that balloon 54 does not perform any further dilatation within the previously expanded region of the vascular system. The balloon 54 is maintained in an inflated condition with isotope I for an appropriate treatment time. Depending on the treatment time, it may be desirable to undertake repeated inflations and deflations of balloon 54 with isotope I to allow a sufficient level of perfusion to occur in between balloon inflations. Alternatively, it is also contemplated that a balloon configuration utilized with the present system may have varying provisions for perfusion of blood flow past balloon 54. This may be accomplished by separate perfusion chambers extending through balloon 54 or altering the surface of balloon 54 slightly to provide irregularities or minimal perfusion channels extending along the length thereof to the extent that it would not compromise uniform dosimetry of the surrounding tissue.

Figure 9:
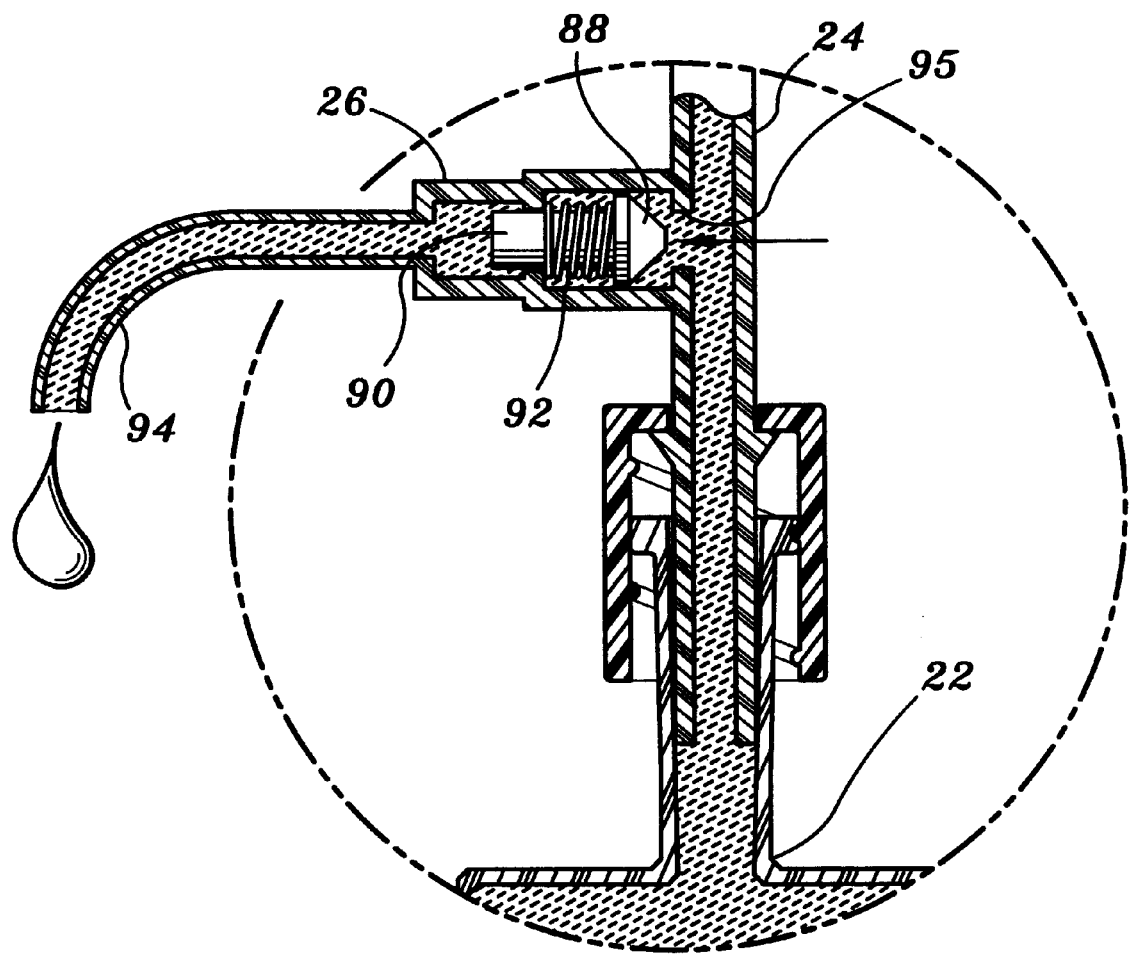
FIG. 9 is an enlarged view of the pressure relief valve associated with the inflation device in operation.

Referring now to FIG. 9, as noted above, pressure in inflation device 24 is maintained at a predetermined level such that the pressure of the isotope fluid within balloon 54 does not exceed another known and predetermined level. However, there is provided pressure relief valve 26 which, when the pressure of saline exceeds a predetermined level, will allow seal 88 to compress spring 92 thereby allowing saline S to pass through pressure relief valve 26 and be siphoned off through drain tube 94. In this manner, over pressurization of balloon 54 may be avoided.

When the procedure is completed, device for radiation therapy 12 may be removed to a shielded container or safe for safe deactivation, disassembly and disposal.

Referring now to FIGS. 10 and 10A, an alternative balloon catheter 130 is provided for use with the above-described system. Balloon catheter 130 is of "rapid exchange" style. Balloon catheter 130 generally includes a catheter shaft 132 having a balloon 134 mounted on a distal end 136 of catheter shaft 132. A guide wire lumen 138 extends from a distal port 140 formed in a distalmost end 142 of catheter shaft 134 and extends proximally beyond the length of the balloon to a proximal port 144 formed proximally of balloon 134. It is also contemplated that the entire guide wire lumen including distal and proximal guide wire ports be located entirely distal of balloon 134.

In order to form the relatively short guide wire lumen 138 extending along the length of balloon 134, a plug 146 is provided within guide wire lumen 138. Plug 146 defines a second lumen 148 which extends from plug 146 proximally to a proximalmost end 150 of catheter shaft 132. By continuing a lumen from plug 146 to the proximalmost end 152 of catheter shaft 132, lumen 148 is configured to receive a separate stiffening mandrel which may be inserted into lumen 148 to facilitate insertion of balloon catheter 18 along guide wire 126 as it is maneuvered through a patient's vascular system.

Balloon catheter 130 is generally affixed to mounting block 20 in the same manner as that of balloon catheter 18 described hereinabove. Specifically, a threaded cap 152 is configured to engage threads 104 formed in a distal end 106 of mounting block 20.

It will be understood that various modifications may be made to the disclosed embodiments. For example, various balloon configurations to provide uniform irradiation of tissue may be provided. Alternatively, multiple balloons may be used. Further, mounting block 20 and transfer device 22 may be modified to allow use thereof with standard known balloon angioplasty catheters thereby allowing the balloon angioplasty catheter to remain in place as air is aspirated out of the catheter and isotope is subsequently injected into the balloon thereby reexpanding the balloon into contact with surrounding tissue to provide uniform irradiation of the tissue. Additionally, alternative isotopes may be utilized depending upon the particular dosage required and half life of the isotope. Thus, the above description should not be construed as limiting, but merely as exemplifications of preferred embodiments. Those skilled in the art will envision other modifications within the scope and spirit of the claims appended hereto.

What is claimed is:

1. A device for radiation therapy of a vascular system comprising:
    a transfer device defining a first chamber at a first end thereof and a second chamber adjacent the first chamber, the transfer device having a piston movably mounted therein and separating the first and second chambers;
    an inflation device removably engagable with the first end of the transfer device, the inflation device containing a first fluid transferable to the first chamber of the transfer device;
    a catheter having an inflatable balloon adjacent a distal end of the catheter and defining an inflation lumen extending from the balloon to a location adjacent a proximal end of the catheter;
    mounting structure removably associated with the balloon catheter and having a fluid chamber in fluid communication with the inflation lumen, the mounting structure being removably engagable with a second end of the transfer device such that the fluid chamber of the mounting structure is in fluid communication with the second chamber of the transfer device; and
    a radioactive fluid located in the second chamber of the transfer device and movable between the second chamber and the balloon in response to movement of the piston.

2. The device as recited in claim 1, wherein the first chamber of the transfer device has a first predetermined cross-sectional area and the second chamber of the transfer device has a second predetermined cross-sectional area different from the first predetermined volume.

3. The device as recited in claim 2, wherein the piston includes a first piston head movably mounted within the first chamber and a second piston head movably mounted within the second chamber.

4. The device as recited in claim 3, wherein the transfer device includes an injection needle extending from the second chamber.

5. The device as recited in claim 4, wherein the needle is surrounded by an elastomeric boot.

6. The device as recited in claim 4, wherein the transfer device has a needle shield extending from the second chamber to the second end of the transfer device.

7. The device as recited in claim 6, wherein the needle shield includes a bayonet mount engagable with a corresponding bayonet mount structure on the mounting structure.

8. The device as recited in claim 4, wherein the mounting structure is a mounting block having a self-sealing septum, the septum configured to seal about the injection needle.

9. The device as recited in claim 8, wherein the mounting block includes a chamber in fluid communication with the inflation lumen of the catheter.

10. The device as recited in claim 9, wherein the mounting block has an injection port in fluid communication with the chamber, the septum of the mounting block being mounted on the injection port.

11. The device as recited in claim 8, wherein the mounting block is connected to the second chamber of the transfer device with a proprietary interlock that is electronically coded with respect to the catheter size and function.

12. The device as recited in claim 1, further comprising an over pressure relief valve mounted on the inflation device.

13. The device as recited in claim 1, wherein the radioactive fluid includes a beta or gamma emitting radio isotope in liquid or gas form.

14. The device as recited in claim 1, wherein the catheter includes a guide wire lumen extending from a first guide wire port at the distal end of the catheter to a proximal guide wire port located proximal to the balloon.

15. The device as recited in claim 1, wherein the proximal guide wire port is adjacent the proximal end of the catheter.

16. The device as recited in claim 1, wherein the first fluid is saline.

17. A method of irradiating vascular tissue comprising the steps of:
    providing a balloon catheter, an inflation device and a transfer device, the transfer device having a first chamber and a second chamber and a piston or membrane movably mounted between the first and second chambers;
    drawing a radioactive fluid into the second chamber of the transfer device;
    inserting the balloon catheter into a vascular system such that a balloon associated with the catheter is positioned at stenotic site;

attaching the balloon catheter to the transfer device such that an inflation lumen of the catheter is in fluid communication with the second chamber of the transfer device;

connecting the inflation device to the transfer device such that the inflation device is in fluid communication with the first chamber of the transfer device;

injecting fluid from the inflation device into the first chamber of the transfer device to move the piston or membrane within the transfer device thereby moving the piston or membrane within the second chamber to force the radioactive fluid out of the second chamber and into the inflation lumen to inflate the balloon.

18. The method as recited in claim 17, wherein the step of drawing a radioactive fluid includes the steps of connecting the first chamber of the transfer device to the inflation device, bringing a source of radioactive fluid into fluid communication with the second chamber of the transfer device and actuating the inflation device to apply negative pressure in the first chamber thereby drawing the piston to create a negative pressure in the second chamber to draw the radioactive fluid out of the source of radioactive fluid and into the second chamber, thereafter disconnecting the transfer device from the inflation device and the source of radioactive fluid.

19. The method as recited in claim 17, further comprising the step of creating a vacuum in the balloon and inflation lumen prior to the step of inserting the balloon catheter into the vascular system.

20. The method as recited in claim 17, wherein the step of attaching includes affixing a proximal end of the balloon catheter to a mounting block and affixing the transfer device to the mounting block such that the second chamber of the transfer device is in fluid communication with the inflation lumen of the balloon catheter through the mounting block.

21. The method as recited in claim 17, further comprising the step of providing adequate shielding for the operator and the patient, such shielding being incorporated into at least said balloon catheter.

* * * * *

UNITED STATES PATENT AND TRADEMARK OFFICE
CERTIFICATE OF CORRECTION

PATENT NO. : 5,961,439
DATED : October 5, 1999
INVENTOR(S) : Ary S. Chernomorsky et al.

It is certified that error appears in the above-identified patent and that said Letters Patent is hereby corrected as shown below:

Title page,
Under Related U.S. Application Data, delete "Provisional application No. 60/077,294", insert -- Provisional Application No. 60/071,342 --.

Signed and Sealed this

Thirtieth Day of April, 2002

*Attest:*

JAMES E. ROGAN
*Attesting Officer*  *Director of the United States Patent and Trademark Office*